US00PP28252P2

(12) United States Plant Patent
Dekker

(10) Patent No.: US PP28,252 P2
(45) Date of Patent: Aug. 8, 2017

(54) ***CHRYSANTHEMUM* PLANT NAMED 'DEKKENNEDY'**

(50) Latin Name: *Chrysanthemum×morifolium*
Varietal Denomination: Dekkennedy

(71) Applicant: DEKKER BREEDING B.V., Hensbroek (NL)

(72) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 40 days.

(21) Appl. No.: 14/998,343

(22) Filed: Jan. 4, 2016

(51) Int. Cl.
*A01H 5/02* (2006.01)

(52) U.S. Cl.
USPC ..... Plt./294

(58) Field of Classification Search
USPC ..... Plt./294
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'Dekkennedy', characterized by single-type inflorescences with white-colored ray florets and bright green-colored disc florets; vigorous growth habit; strong and upright flowering stems; relatively short response time; uniform and freely flowering habit; and good postproduction longevity; plants maintain good substance for about 19 days in an interior environment.

2 Drawing Sheets

Botanical designation: *Chrysanthemum×morifolium.*
Cultivar denomination: 'DEKKENNEDY'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Dekkennedy'.

The new *Chrysanthemum* plant is a product of a planned breeding program conducted by the Inventor in Hensbroek, The Netherlands. The objective of the breeding program is to create new freely-flowering cut *Chrysanthemum* plants with single inflorescences, strong flowering stems, short response time and excellent postproduction longevity.

The new *Chrysanthemum* plant originated from a cross-pollination made by the Inventor in Hensbroek, The Netherlands in September, 2012, of a proprietary selection of *Chrysanthemum×morifolium* identified as code number 09.92062.01, not patented, as the female, or seed, parent with a proprietary selection of *Chrysanthemum×morifolium* identified as code number 08.81756.01, not patented, as the male, or pollen, parent. The new *Chrysanthemum* plant was discovered and selected by the Inventor as a single flowering plant from within the progeny of the stated cross-pollination in a controlled greenhouse environment in Hensbroek, The Netherlands in April, 2013.

Asexual reproduction of the new *Chrysanthemum* plant by terminal cuttings in a controlled greenhouse environment in Hensbroek, The Netherlands since May, 2013 has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dekkennedy'. These characteristics in combination distinguish 'Dekkennedy' as a new and distinct *Chrysanthemum* plant:

1. Single-type inflorescences with white-colored ray florets and bright green-colored disc florets.
2. Vigorous growth habit.
3. Strong and upright flowering stems.
4. Relatively short response time.
5. Uniform and freely flowering habit.
6. Good postproduction longevity; plants maintain good substance for about 19 days in an interior environment.

Plants of the new *Chrysanthemum* differ from plants of the female parent selection in the following characteristics:

1. Plants of the new *Chrysanthemum* flower about three days earlier than plants of the female parent selection.
2. Plants of the new *Chrysanthemum* and the female parent selection differ in ray floret color as plants of the female parent selection have pink-colored ray florets.

Plants of the new *Chrysanthemum* differ from plants of the male parent selection in the following characteristics:

1. Plants of the new *Chrysanthemum* are more vigorous than plants of the male parent selection.
2. Plants of the new *Chrysanthemum* have slightly smaller than plants of the male parent selection.

Plants of the new *Chrysanthemum* can be compared to plants of *Chrysanthemum×morifolium* 'Bacardi', not patented. In side-by-side comparisons conducted in Hensbroek, The Netherlands, plants of the new *Chrysanthemum* differed from plants of 'Bacardi' in the following characteristics:

1. Plants of the new *Chrysanthemum* were more vigorous than plants of 'Bacardi'.

2. Plants of the new *Chrysanthemum* flowered about three days earlier than plants of 'Bacardi'.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Dekkennedy' grown as a spray-type.

The photograph on the second sheet comprises close-up views of the upper (top of the photograph) and lower surfaces (bottom of the photograph) of typical inflorescences and leaves of 'Dekkennedy'.

DETAILED BOTANICAL DESCRIPTION

The aforementioned photographs and following observations and measurements describe plants grown during the autumn in ground beds in a glass-covered greenhouse in Hensbroek, The Netherlands and under cultural practices typical of commercial cut *Chrysanthemum* production. Plants were initially given twelve days of long day/short night treatments followed by short day/long night treatments to induce flower initiation and development. During the production of the plants, day temperatures ranged from 18° C. to 30° C., night temperatures ranged from 18° C. to 20° C. and light levels averaged 10,000 lux. Plants were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum×morifolium* 'Dekkennedy'.

Parentage:

*Female, or seed, parent*.—Proprietary selection of *Chrysanthemum×morifolium* identified as code number 09.92062.01, not patented.

*Male, or pollen, parent*.—Proprietary selection of *Chrysanthemum×morifolium* identified as code number 08.81756.01, not patented.

Propagation:

*Type*.—Terminal vegetative cuttings.

*Time to initiate roots, summer*.—About four days at 20° C.

*Time to initiate roots, winter*.—About six days at 20° C.

*Time to produce a rooted young plant, summer*.—About 13 days at 20° C.

*Time to produce a rooted young plant, winter*.—About 15 days at 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous single-type cut flower that is typically grown as a spray-type; upright plant habit; vigorous growth habit and rapid growth rate.

*Plant height, soil level to top of foliar plane*.—About 74 cm.

*Plant height, soil level to top of flower plane*.—About 82 cm.

*Plant (spray) diameter*.—About 21.6 cm.

*Flowering stem diameter*.—About 3.5 mm.

*Flowering stem internode length*.—About 3.3 cm.

*Flowering stem strength*.—Strong.

*Flowering stem aspect*.—Erect.

*Flowering stem texture and luster*.—Densely pubescent; longitudinally ridged; glossy.

*Flowering stem color, developing*.—Close to 138B.

*Flowering stem color, developed*.—Close to 144A to 144C.

*Leaf description*.—Arrangement: Alternate; simple. Length: About 8.2 cm. Width: About 5.8 cm. Shape: Ovate. Apex: Broad and short apiculate. Base: Truncate to attenuate. Margin: Palmately lobed, coarsely serrate; sinuses convergent. Texture and luster, upper surface: Densely pubescent, slightly rugose; moderately velvety; matte. Texture and luster, upper surface: Densely pubescent, prominent venation; slightly to moderately velvety; slightly glossy. Venation pattern: Pinnate, reticulate. Color: Developing leaves, upper surface: Close to 137A. Developing leaves, lower surface: Close to 137D. Fully developed leaves, upper surface: Close to NN137D; venation, close to 137C. Fully developed leaves, lower surface: Close to 138B; venation, close to 138B. Petioles: Length: About 9 mm. Diameter: About 2.5 mm by 5 mm. Strength: Moderately strong. Texture and luster, upper and lower surfaces: Moderately to densely pubescent; matte. Color, upper surface: Close to 138B; edges, close to NN137D. Color, lower surface: Close to 138B; edges, close to 137C. Stipules: Quantity and appearance: Two leafy stipules, opposite, at the petiole attachment to the stem. Length: About 1 cm. Width: About 9 mm. Texture and luster, upper surface: Densely pubescent; matte. Texture and luster, upper surface: Densely pubescent; slightly glossy. Color, upper surface: Close to NN137D. Color, lower surface: Close to 138B.

Inflorescence description:

*Appearance*.—Single-type inflorescence form with obovate-shaped ray florets and tubular disc florets; inflorescences borne perpendicular to peduncles; ray and disc florets develop acropetally on a capitulum.

*Fragrance*.—Faintly fragrant.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 48 days later when grown as a spray-type.

*Postproduction longevity*.—Good postproduction longevity; in an interior environment, inflorescences and foliage will maintain good color and substance for about 19 days; inflorescences persistent.

*Quantity of inflorescences*.—Freely flowering habit; when grown as a spray type, about 31 inflorescences develop per flowering stem.

*Inflorescence size*.—Diameter: About 7.4 cm. Depth (height): About 2.4 cm. Disc diameter: About 2 cm.

*Receptacles*.—Height: About 4 mm. Diameter: About 5.5 mm. Shape: Flattened globular. Color: Close to 145C.

*Inflorescence buds*.—Height: About 1 cm. Diameter: About 1.1 cm. Shape: Broadly ovoid. Texture and luster: Smooth, glabrous; slightly glossy. Color: Close to 143A; towards the apex, close to 155C.

*Ray florets*.—Quantity and arrangement: About 34 arranged in about three whorls. Length: About 3.2 cm. Width: About 1.4 cm. Shape: Obovate; slightly carinate. Apex: Obtuse to shallowly praemorse. Base: Attenuate. Margin: Entire; slightly undulate. Aspect: Initially upright to about 75° from vertical. Texture and luster, upper surface: Smooth, glabrous; velvety; matte to very slightly glossy. Texture and luster, lower surface: Smooth, glabrous; Aspect: About 20° from horizontal. Color: When opening, upper surface: Close to NN155D. When opening, lower surface: Close to NN155B. Fully opened, upper and lower surfaces: Close to NN155D.

*Disc florets*.—Quantity and arrangement: About 240 spirally arranged in about ten whorls at the center of the receptacle. Length: About 6.75 mm. Diameter: About 2 mm. Shape: Fused tubular, erect and elongated. Apex: Upper 12% free, acute. Texture and luster, inner and outer surfaces: Smooth, glabrous; glossy. Color, when opening, inner and outer surfaces: Apex: Close to 144C. Mid-section: Close to 150D. Base: Close to 145D. Color, fully opened, inner and outer surfaces: Apex: Close to N144B. Mid-section and base: Close to 145C.

*Involucral bracts*.—Quantity and arrangement: About 24 arranged in two whorls. Length: About 8 mm. Width: About 4 mm. Shape: Ovate. Apex: Acute. Base: Cuneate. Margin: Entire. Texture and luster, upper surface: Smooth, glabrous; glossy. Texture and luster, lower surface: Densely pubescent; matte. Color, upper surface: Close to 143A. Color, lower surface: Close to NN137A.

*Peduncles*.—Length, terminal peduncle: About 1.8 cm. Diameter, terminal peduncle: About 3 mm. Length, third peduncle: About 5.5 cm. Diameter, terminal peduncle: About 3 mm. Strength: Strong. Aspect, terminal peduncle: Mostly upright. Aspect, third peduncle: About 30° from the flowering stem axis. Texture and luster: Densely pubescent; slightly glossy. Color: Close to 143B.

*Reproductive organs*.—Androecium: Present on disc florets only. Quantity: About five per floret. Filament length: About 2 mm. Filament color: Close to 145D. Anther size: About 0.3 mm by 1.5 mm. Anther shape: Narrowly oblong. Anther color: Close to 13A. Pollen amount: Scarce. Pollen color: Close to 13A. Gynoecium: Present on both ray and disc florets. Quantity: One per floret. Pistil length: About 6 mm. Style length: About 5 mm. Style color: Close to N144B. Stigma diameter: About 1.5 mm. Stigma shape: Cleft, decurrent. Stigma color: Close to 12A. Ovary color: Close to 145D.

*Seeds and fruits*.—Seed and fruit production have not been observed on plants of the new *Chrysanthemum*.

Disease & pest resistance: Resistance to pathogens and pests common to *Chrysanthemum* plants has not been observed on plants of the new *Chrysanthemum* grown under commercial conditions.

Temperature tolerance: Plants of the new *Chrysanthemum* have been observed to tolerate temperatures ranging from about −12° C. to 35° C.

It is claimed:

1. A new and distinct *Chrysanthemum* plant named 'Dekkennedy' as illustrated and described.

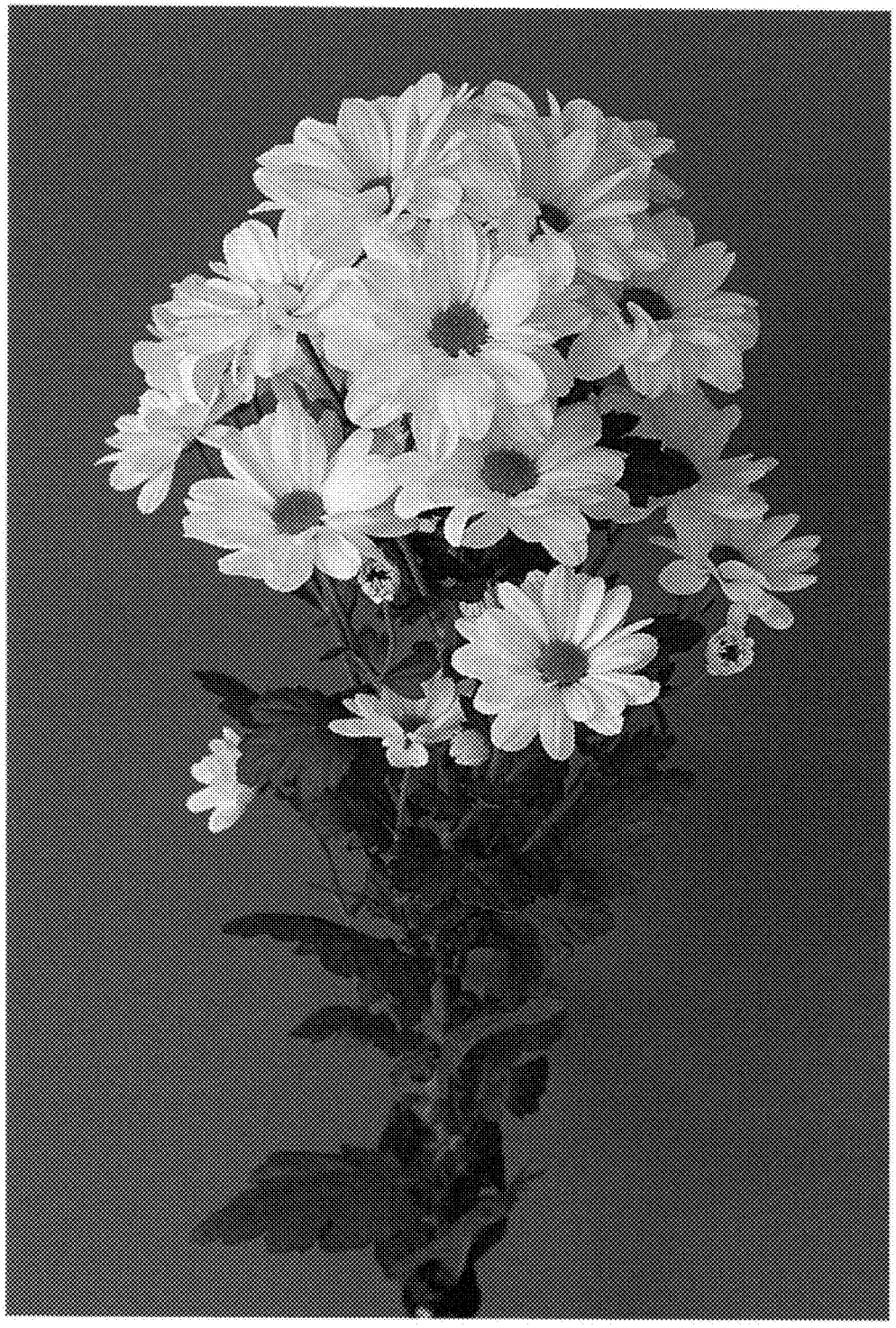

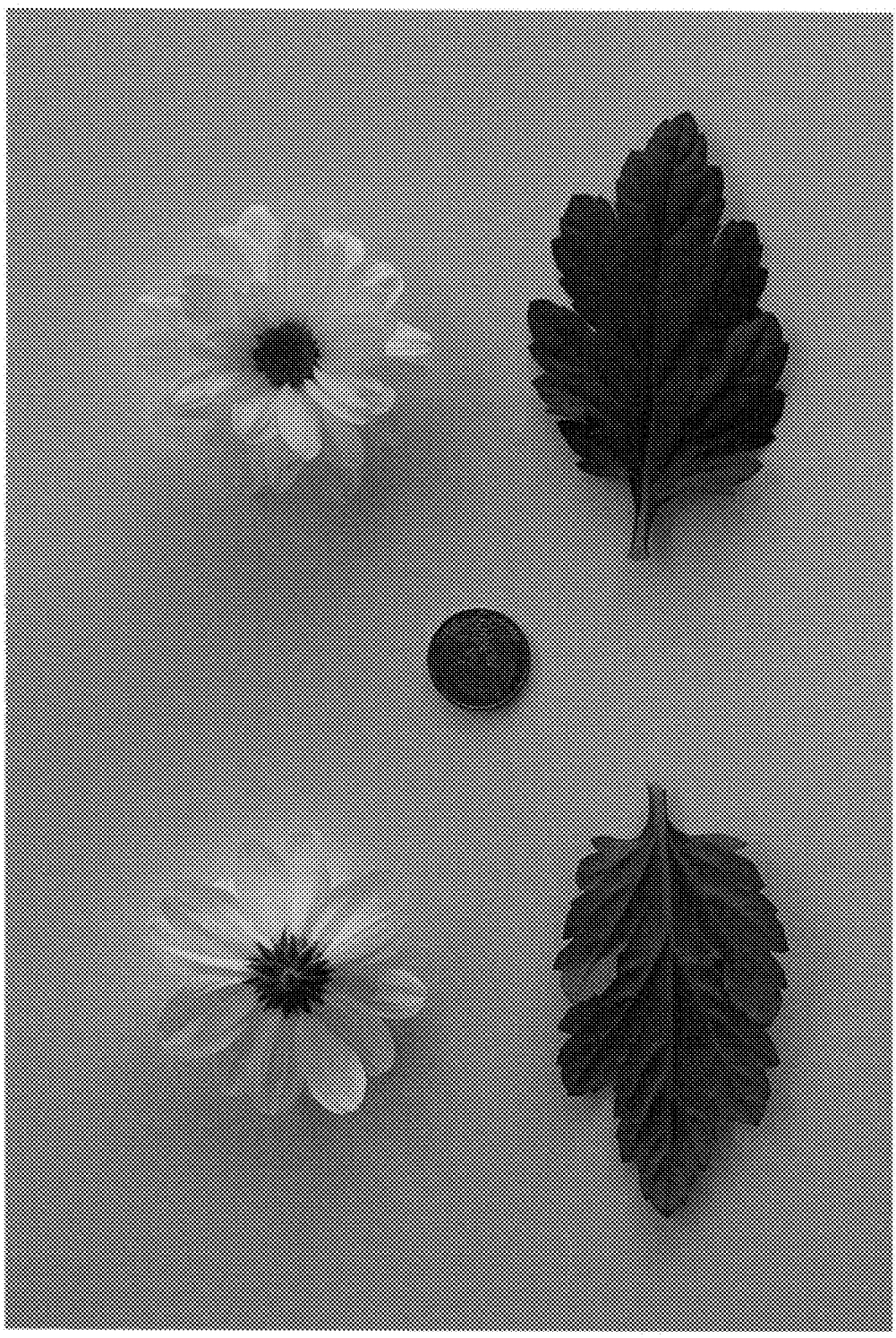

* * * * *